(12) United States Patent
Goldbach et al.

(10) Patent No.: US 8,334,319 B2
(45) Date of Patent: Dec. 18, 2012

(54) POLYMORPHIC FORMS OF OSELTAMIVIR PHOSPHATE

(75) Inventors: Pierre Goldbach, Rixheim (FR); Olaf Grassmann, Loerrach (DE); Ines Sauer, Mannheim (DE)

(73) Assignee: Roche Palo Alto LLC, South San Francisco, CA (US)

( * ) Notice: Subject to any disclaimer, the term of this patent is extended or adjusted under 35 U.S.C. 154(b) by 705 days.

(21) Appl. No.: 12/317,157

(22) Filed: Dec. 19, 2008

(65) Prior Publication Data

US 2009/0176886 A1    Jul. 9, 2009

(30) Foreign Application Priority Data

Jan. 4, 2008 (EP) .................................... 08150057

(51) Int. Cl.
*A61K 31/215* (2006.01)
*C07C 229/48* (2006.01)

(52) U.S. Cl. ....................... 514/529; 560/125
(58) Field of Classification Search ........................ None
See application file for complete search history.

(56) References Cited

U.S. PATENT DOCUMENTS

| 5,859,284 | A | 1/1999 | Kent et al. | |
| 2008/0227743 | A1* | 9/2008 | Nguyen et al. | 514/44 |

FOREIGN PATENT DOCUMENTS

| WO | WO 98/07685 A1 | 2/1998 |
| WO | 2008/112775 A1 | 9/2008 |

OTHER PUBLICATIONS

Shie et al, Journal of the American Chemical Society, Synthesis of Tamiflu and it's Phosphonate Congeners Possessing Potent Anti-Influenza Properties, 2007, 129, pp. 11892-11893.*
Billinge et al, CrystEngComm, Characterization of Amorphous and Nanocrystalline Molecular Materials by Total Scattering, 2010, 12, pp. 1366-1368.*
Green et al, Emerging Infectious Diseases, www.cdc.gov/eid, Determination of Oseltamivir Quality by Colorimetric and Liquid Chromatographic Methods, 2008, 14(4), pp. 552-556.*
Bedu-Addo, Pharmaceutical Technology, Lyophilization, Understanding Lyophilization Formula Development, 2004, pp. 10-18, obtained from http://pharmtech.findpharma.com/pharmtech/data/articlestandard//pharmtech/072004/84717/article.pdf.*
Braga et al., "Making crystals from crystals: a green route to crystal engineering and polymorphism" ChemComm 2005, 3635-3645.*
Fututa, Y., et. al. "De Novo Synthesis of Tamiflu via a Catalytic Asymmetric Ring-Opening of meso-Aziridines with TMSN3," JACS, Published on Web Apr. 25, 2006, vol. 128, pp. 6312 and 6313.
Caira, M. R. "Crystalline Polymorphism of Organic Compounds," *Topics in Current Chemistry*, 1998, vol. 198, pp. 163-208.
Fukuta, Y. et. al. "De Novo Synthesis of Tamiflu via a Catalytic Enantioselective Ring-Opening Reaction of meso-Aziridines with TMSN$_3$," *Journal of American Chemical Society*, 2006, online pp. S1-S15.
Communication Pursuant to Article 94(3) EPC for European Application No. 08 869 959.0-1211 dated Nov. 15, 2011.
He et al., "Clinical Pharmacokinetics of the prodrug Oseltamivir and its active metabolites Ro 64-0802" Clin. Pharmacokinet. 36(7):471-484 (Dec. 1999).

* cited by examiner

*Primary Examiner* — Paul A Zucker
(74) *Attorney, Agent, or Firm* — Brian L. Buckwalter (57) ABSTRACT

The present invention relates to polymorphic forms of (3R, 4R,5S)-5-amino-4-acetylamino-3-(1-ethyl-propoxy)-cyclohex-1-ene-carboxylic acid ethyl ester phosphate, which is a potent inhibitor of viral neuraminidase.

9 Claims, 8 Drawing Sheets

POLYMORPHIC FORMS OF OSELTAMIVIR PHOSPHATE

CROSS REFERENCE TO PRIOR APPLICATIONS

This application claims the benefit of priority to EP 08150057.1 filed Jan. 4, 2008 the contents of which are hereby incorporated in their entirety by reference.

FIELD OF THE INVENTION

The present invention relates to new crystalline and amorphous forms of oseltamivir phosphate which are useful for the inhibition of viral neuramidase and treatment of viral infections. The new crystalline and amorphous forms of oseltamivir phosphate afford forms that can be conveniently formulated.

BACKGROUND OF THE INVENTION

Oseltamivir phosphate is (3R,4R,5S)-5-amino-4-acetylamino-3-(1-ethyl-propoxy)-cyclohex-1-enecarboxylic acid ethyl ester phosphate ula (I) which is

I disclosed by J. C. Rohloffet al, *J. Org. Chem.* 1998 63: 4545-4550 and WO 98/07685 has a potent inhibitory activity against virus neuraminidase and is useful for prevention and/or treatment of influenza virus infections. It is the active ingredient of Tamiflu (Registered Trade Mark).

Crystalline form A of the compound of formula I, is characterized by an X ray powder diffraction pattern comprising at least three, preferably five, more preferably seven X-ray diffraction peaks (expressed in degrees 2θ (degrees 2-theta)) selected from the group consisting of approximately 5.1, approximately 12.4, approximately 13.0, approximately 14.3, approximately 15.2, approximately 16.1, approximately 19.0, approximately 19.3, approximately 20.3, approximately 20.6, approximately 21.6, approximately 24.4 and approximately 26.3.

Figure 1:
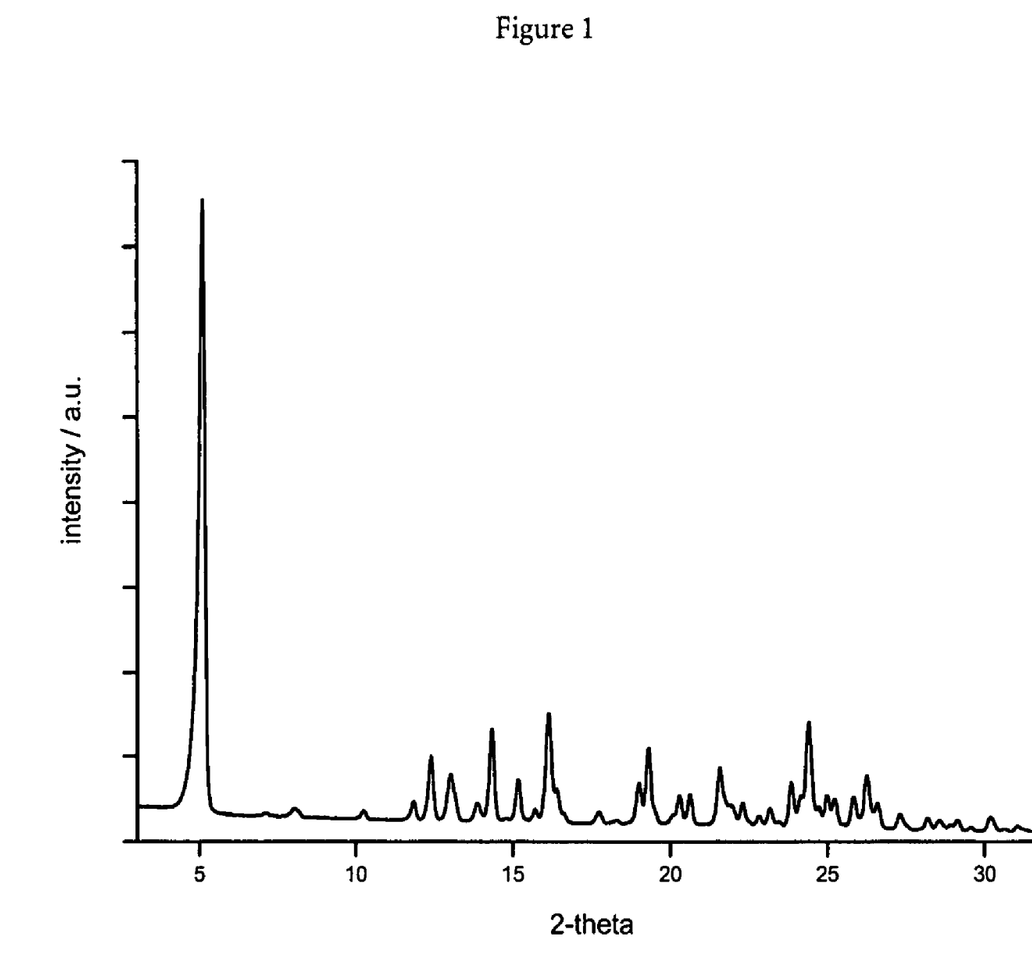
FIG. 1 shows a XRPD pattern of form A of (3R,4R,5S)-4-acetylamino-5-amino-3-(1-ethyl-propoxy)-cyclohex-1-enecarboxylic acid ethyl ester phosphate.
Figure 2:
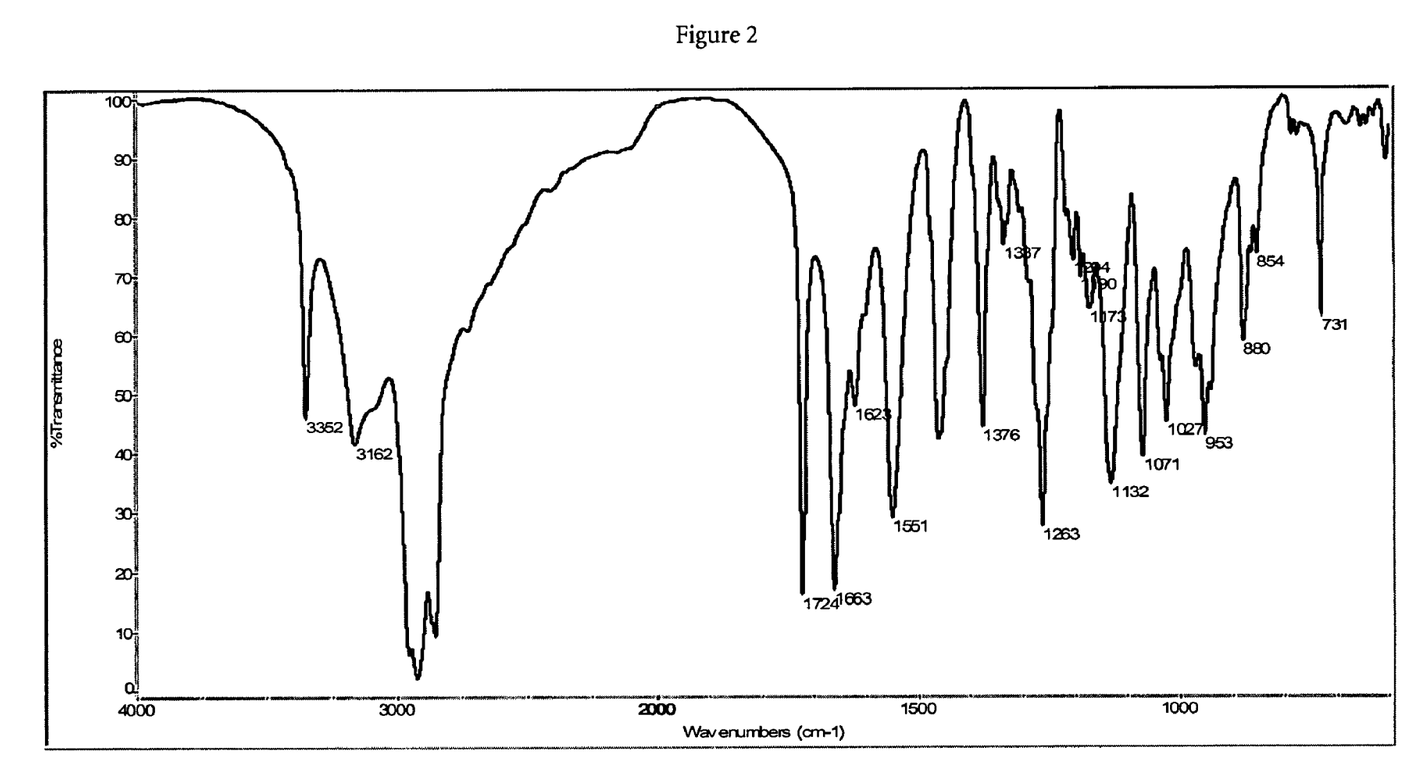
FIG. 2 shows an IR (InfraRed spectroscopy) spectrum of form A of (3R,4R,5S)-4-acetylamino-5-amino-3-(1-ethyl-propoxy)-cyclohex-1-enecarboxylic acid ethyl ester phosphate.
Figure 3:
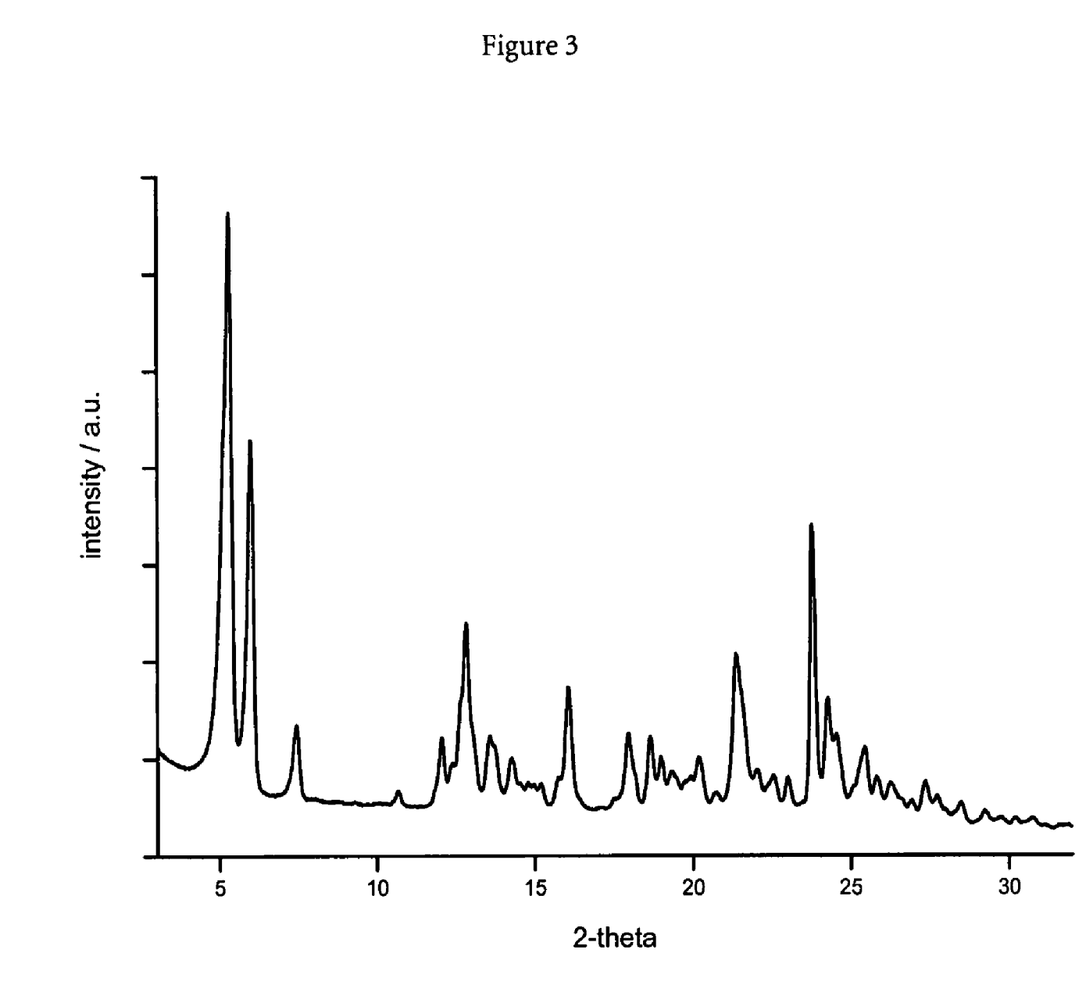
FIG. 3 shows a XRPD pattern of form B of (3R,4R,5S)-4-acetylamino-5-amino-3-(1-ethyl-propoxy)-cyclohex-1-enecarboxylic acid ethyl ester phosphate.
Figure 4:
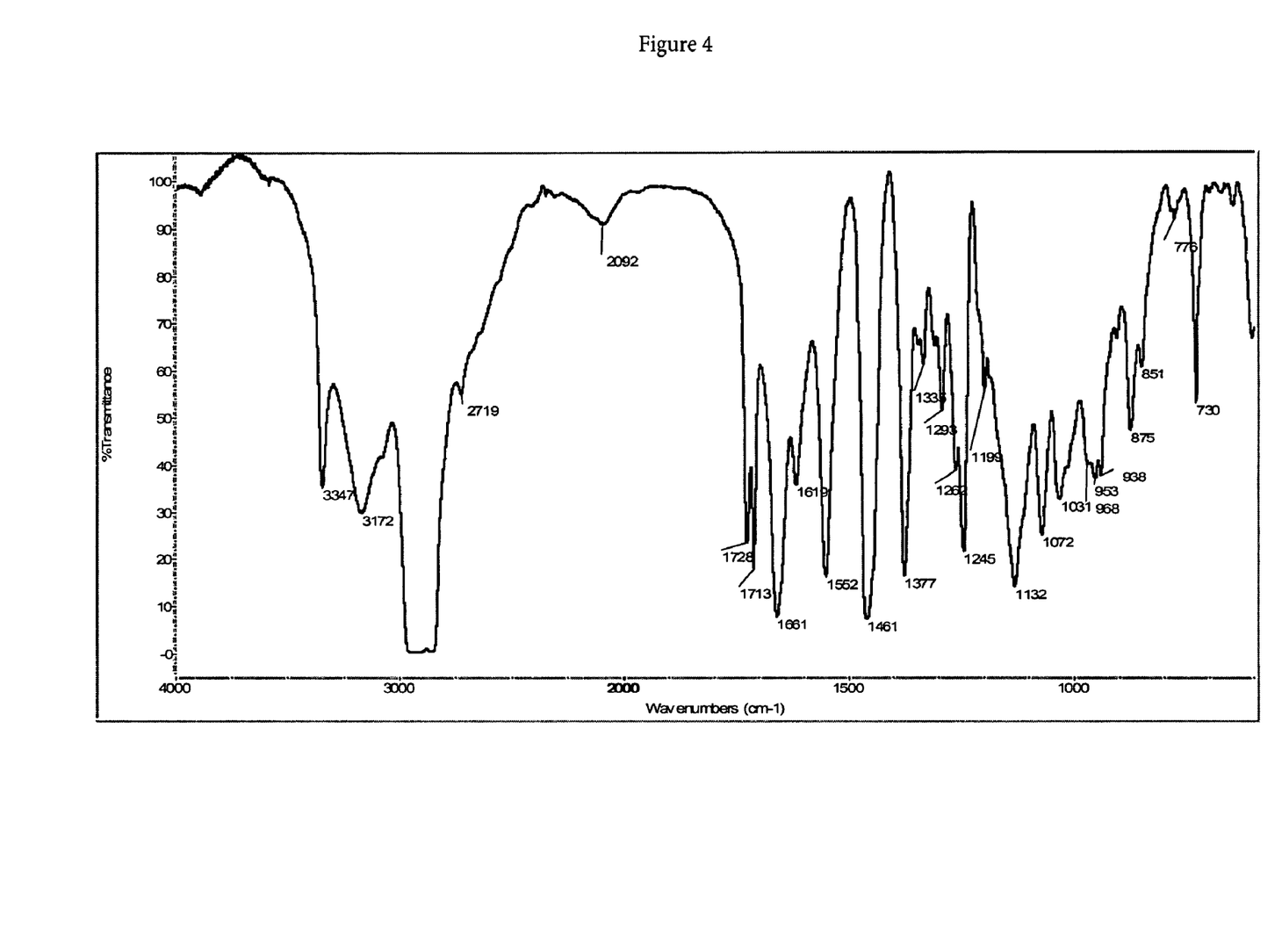
FIG. 4 shows an IR spectrum of form B of (3R,4R,5S)-4-acetylamino-5-amino-3-(1-ethyl-propoxy)-cyclohex-1-enecarboxylic acid ethyl ester phosphate.
Figure 6:
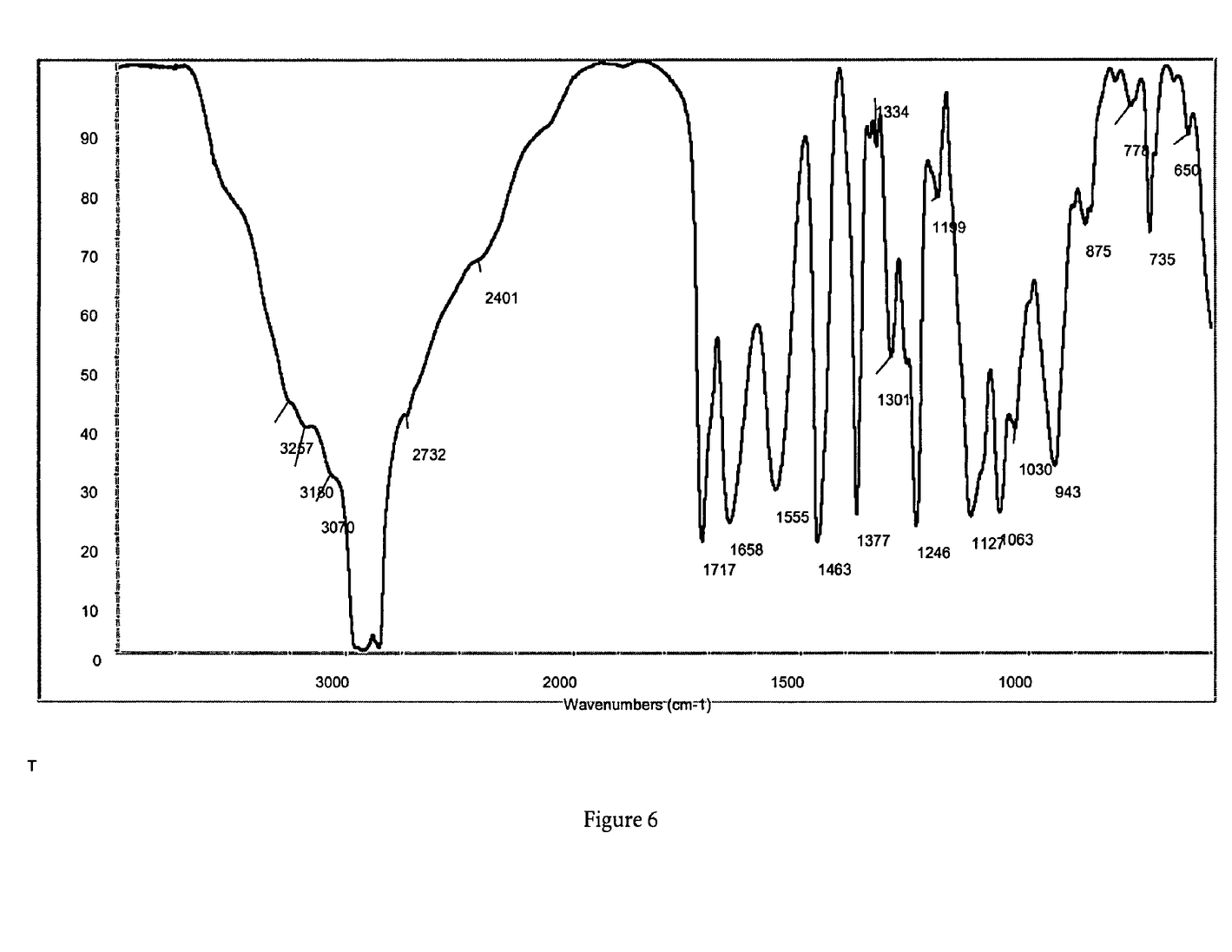
FIG. 6 shows an IR spectrum of an amorphous form of (3R,4R,5S)-4-acetylamino-5-amino-3-(1-ethyl-propoxy)-cyclohex-1-enecarboxylic acid ethyl ester phosphate.
Figure 7:
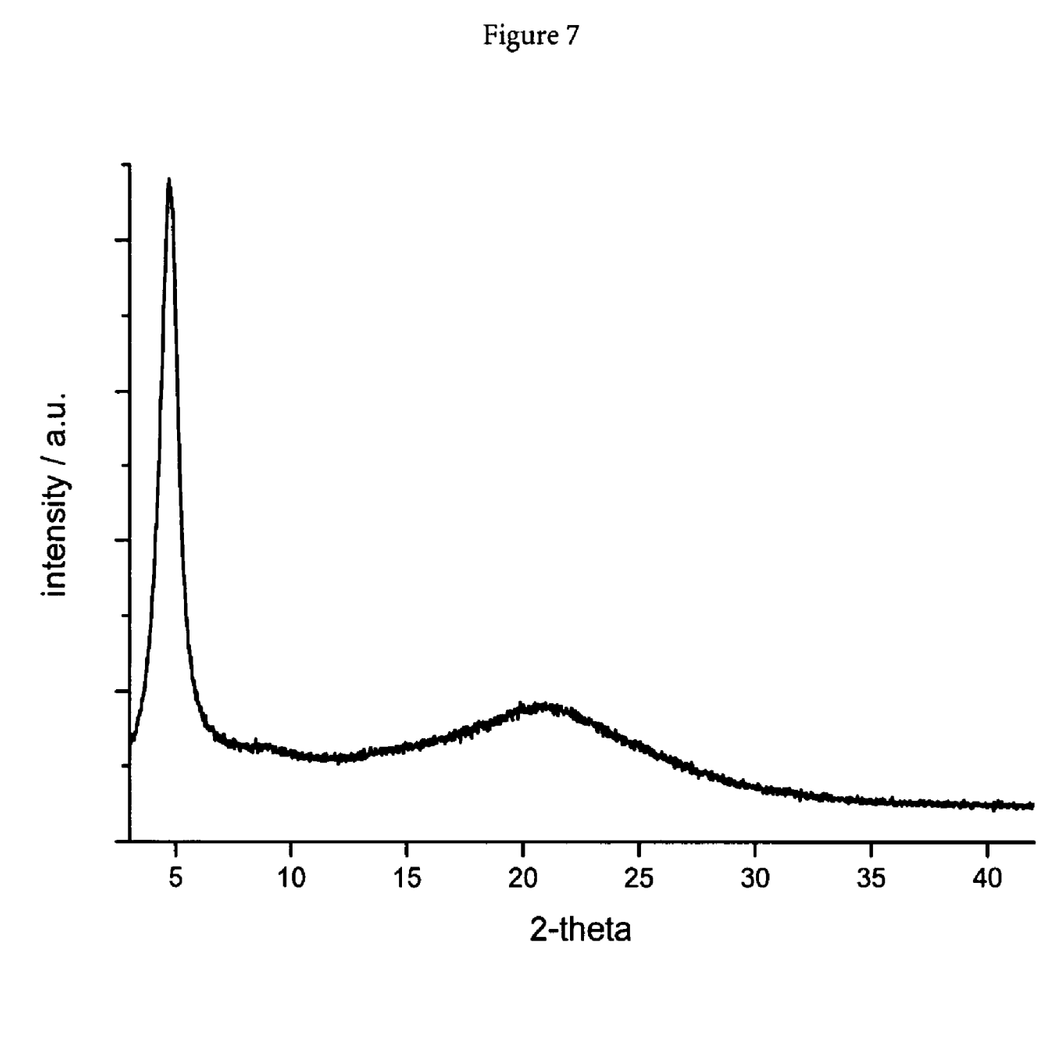
FIG. 7 shows a XRPD pattern of an amorphous form of (3R,4R,5S)-4-acetylamino-5-amino-3-(1-ethyl-propoxy)-cyclohex-1-enecarboxylic acid ethyl ester phosphate.
Figure 8:
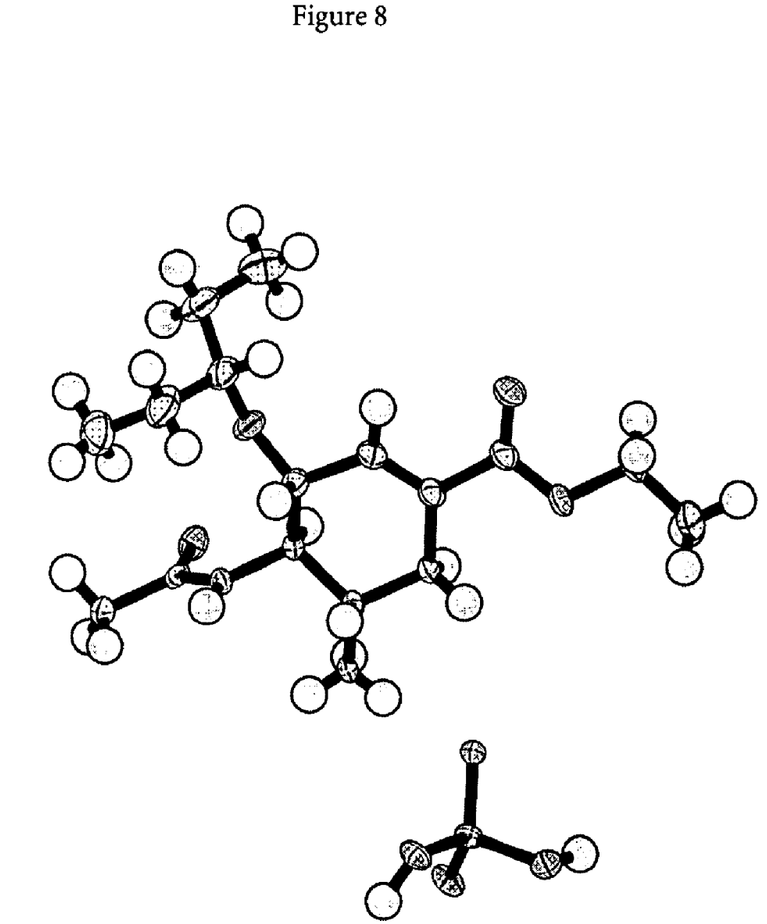
FIG. 8 shows a thermal ellipsoid plot of the crystal structure of form A
Figure 51:
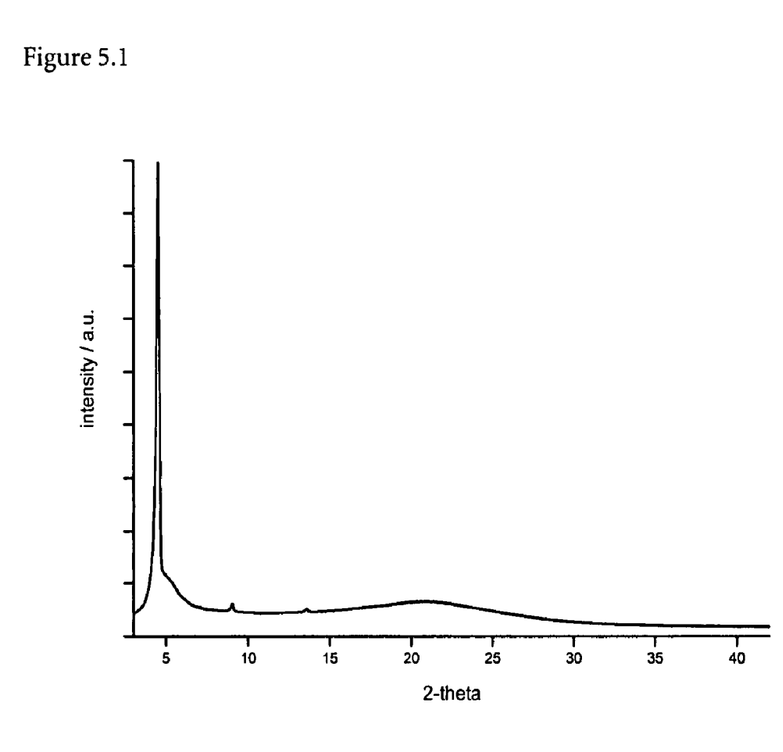
Figure 52:
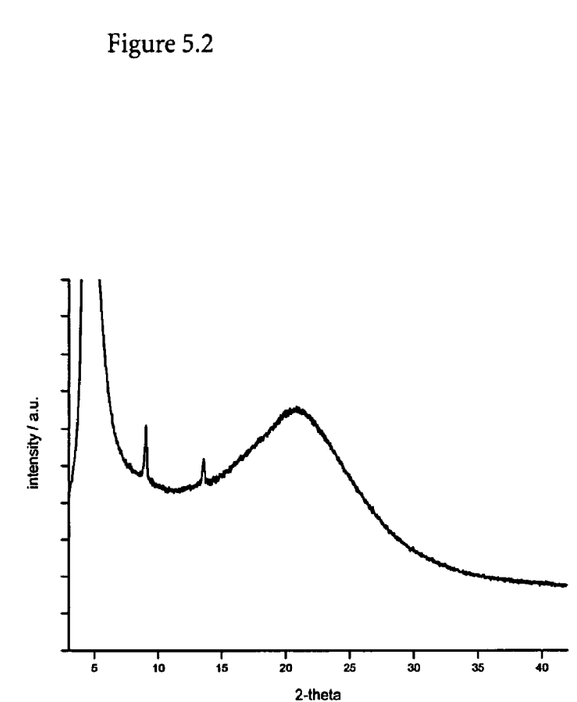

A single crystal structural analysis of form A was conducted. Table 1 lists the crystal structure data. The experimental X-ray powder diffraction (XRPD) pattern collected with the form A corresponds to the theoretical pattern calculated from crystal structure data. The absolute configuration of the molecules was determined from single crystal structure data. The crystal packing of form A shows hydrogen bonds of the protonated amino group to three phosphate molecules. The amide oxygen accepts a hydrogen from another phosphate molecule. Consequently, the phosphate molecule forms hydrogen bonds to four different molecules of the active molecule. This results a hydrogen bonding pattern of tightly bond columns parallel to the crystallographic c-axis. A thermal ellipsoid plot of the crystal structure is shown in FIG. 8.

TABLE 1

| Crystal structure data of form A | |
|---|---|
| form | A |
| crystal system | orthorhombic |
| space group | P 2(1) 2(1) 2 |
| crystal habit | needle |
| unit cell dimensions | a = 23.8 Å |
|  | b = 24.4 Å |
|  | c = 7.4 Å |
|  | α, β, γ = 90.0° |
| temperature | 89° K |
| cell volume | 4289 Å$^3$ |
| molecules in unit cell | 8 |
| calculated density | 1.27 g/cm$^3$ |

For single crystal structure analysis a single crystal was mounted in a loop on a goniometer and measured at ambient conditions. Alternatively, the crystal was cooled in a nitrogen stream during measurement. Data were collected on a STOE Imaging Plate Diffraction System (IPDS) from STOE (Darmstadt). In this case Mo-radiation of 0.71 Å wavelength was used for data collection. Data was processed with STOE IPDS-software. The crystal structure was solved and refined with the ShelXTL program from Bruker AXS (Karlsruhe).

Alternatively, synchrotron radiation was used for data collection. A single crystal was mounted in a loop and cooled to 100 K in a nitrogen stream. Data was collected at the Swiss Light Source beamline XIOSA using a MAR CCD225 detector with synchrotron radiation and data processed with the program XDS. The crystal structure was solved and refined with the ShelXTL program from Bruker AXS (Karlsruhe).

The active pharmaceutical ingredient of the commercially available medicament Tamiflu is in crystalline form A.

SUMMARY OF THE INVENTION

The present invention relates to polymorphic or amorphous forms (3R,4R,5S)-5-amino-4-acetylamino-3-(1-ethyl-propoxy)-cyclohex-1-ene-carboxylic acid ethyl ester phosphate (I), which is a potent inhibitor of viral neuraminidase useful for treatment or prevention of influenza. There are provided two polymorphic crystalline forms along with amorphous oseltamivir phosphate (I) useful for preparing pharmaceutical formulations

BRIEF DESCRIPTION OF THE FIGURES

FIG. 5.1 shows a XRPD pattern of form C of (3R,4R,5S)-4-acetylamino-5-amino-3-(1-ethyl-propoxy)-cyclohex-1-enecarboxylic acid ethyl ester phosphate.

FIG. 5.2 rescaled XRPD pattern of FIG. 5.1.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The specific crystalline forms of (3R,4R,5S)-4-acetylamino-5-amino-3-(1-ethyl-propoxy)-cyclohex-1-enecarboxylic acid ethyl ester phosphate (I) are herein referred to as "crystalline form A", "crystalline form B" and "crystalline form C".

In an embodiment of the present invention there is provided a new crystalline form B of the compound of formula I, which is characterized by an XRPD pattern comprising at least three peaks (expressed in degrees 2θ) selected from the group consisting of approximately 5.3, approximately 6.0, approximately 7.4, approximately 12.1, approximately 12.8, approximately 13.6, approximately 16.1, approximately 18.0, approximately 18.7, approximately 21.4, approximately 23.8 and approximately 24.3. In another embodiment of the present invention there is provided a crystalline Form B characterized by at least five XRPD peaks from the above list. In still another embodiment of the present invention there is provided a crystalline Form B characterized by at least seven XRPD peaks from the above list.

In an embodiment of the present invention there is provided a new crystalline form C of the compound of formula (I), which is characterized by an XRPD comprising at least one XRPD peak (expressed in degrees 2θ) selected from the group consisting of approximately 4.5, approximately 9.1 and approximately 13.6. In another embodiment of the present invention there is provided a crystalline Form C characterized by at least two XRPD peaks from the above list. In still another embodiment of the present invention there is provided a crystalline Form C characterized by at least three XRPD peaks from the above list.

In an embodiment of the present invention there is provided an amorphous form of the compound of formula I, which is characterized by an XRPD pattern lacking a Bragg diffraction peak. This amorphous form is also characterized by an XRPD pattern comprising one or more amorphous halos.

In an embodiment of the present invention there is provided a pharmaceutical compositions comprising crystalline form B and/or crystalline form C or the above mentioned amorphous of the compound of formula I and a pharmaceutically acceptable excipient.

In an embodiment of the present invention there is provided a method for inhibiting influenza viruses, in particular the selective inhibition of viral neuraminidases comprising administering a therapeutically effective amount of a crystalline form B and/or crystalline form C or the above mentioned amorphous form of the compound of formula I to a patient in need thereof.

Unless otherwise indicated, the following definitions are set forth to illustrate and define the meaning and scope of the various terms used to describe the invention herein.

"Amorphous forms" or "amorphous" denote a material that does not show a Bragg diffraction peak. The XRPD pattern of an amorphous material is also characterized by one or more amorphous halos.

Bragg's law describes the diffraction of crystalline material with the equation:

$$2d \sin \theta = n\lambda$$

wherein d=perpendicular distance between pairs of adjacent planes in a crystal (d-spacing), θ (theta)=Bragg angle, λ (lambda)=wavelength and n=integer.

When Bragg's law is fulfilled, the reflected beams are in phase and interfere constructively so that Bragg diffraction peaks are observed in the X-ray diffraction pattern. At angles of incidence other than the Bragg angle, reflected beams are out of phase and destructive interference or cancellation occurs. Amorphous material does not satisfy Bragg's law and no Bragg diffraction peaks are observed in the X-ray diffraction pattern.

An "amorphous halo" is an approximately bell-shaped diffraction maximum in the X-ray powder diffraction pattern of an amorphous substance. The FWHM of an amorphous halo is in principle bigger than the FWHM of a peak of crystalline material.

"FWHM" means full width at half maximum, which is a width of a peak appearing in an XRPD pattern at its half height.

"Form A" is used herein as abbreviation for the crystalline form A of (3R,4R,5S)-4-acetylamino-5-amino-3-(1-ethyl-propoxy)-cyclohex-1-enecarboxylic acid ethyl ester phosphate.

"Form B" is used herein as abbreviation for the crystalline form B of (3R,4R,5S)-4-acetylamino-5-amino-3-(1-ethyl-propoxy)-cyclohex-1-enecarboxylic acid ethyl ester phosphate.

"Form C" is used herein as abbreviations for the crystalline form C of (3R,4R,5S)-4-acetylamino-5-amino-3-(1-ethyl-propoxy)-cyclohex-1-enecarboxylic acid ethyl ester phosphate.

"IR" is used herein as an acronym of Infrared spectroscopy. IR spectra were recorded as film of a Nujol suspension of approximately 5 mg of sample and few Nujol between two sodium chloride plates, with an FTIR spectrometer in transmittance. The Spectrometer is a Nicolet™ 20SXB or equivalent (resolution 2 $cm^{-1}$, 32 or more coadded scans, MCT detector).

"XRPD (is used herein as an acronym of X-Ray Powder Diffraction)" X-ray diffraction patterns were recorded at ambient conditions in transmission geometry with a STOE STADI P diffractometer (Cu Kα radiation, primary monochromator, position sensitive detector, angular range 3° to 42° 2θ, approximately 60 minutes total measurement time). The samples were prepared and analyzed without further processing (e.g. grinding or sieving) of the substance.

"Excipient" and "pharmaceutically acceptable excipient" mean inactive pharmaceutically acceptable ingredients that are, other than drug substances, not intended to treat and/or prevent illnesses. It is to be understood that the excipients, including, but not limited to, diluents, surfactants, wetting agents, binders, lubricants, disintegrating agents, carriers, fillers, etc. are of pharmaceutically acceptable grade.

"Pharmaceutically active drug substance(s)" and "drug substance(s)" are used interchangeably to denote a pharmaceutically active principle which is intended to treat and/or prevent illnesses.

"Micronization" means the process whereby the particle size of a single drug substance, is diminished by the aid of a suitable mill, e.g. an air-jet mill.

"Co-micronization" means that a mixture comprising at least one drug substance and at least one excipient is micronized in a suitable mill to obtain a diminished particle size of the drug substance.

Throughout this application the term "approximately" in the context of XRPD patterns means that there is an uncertainty in the measurements of the degrees 2θ of +0.2 degrees 2θ. The term "approximately" means, in the context of an infra-red spectra, indicates an uncertainty in the measurements of the wavenumbers of ±3 cm$^{-1}$.

Crystalline forms and amorphous forms of the present invention can be prepared, for example, by the general preparation procedures described below.

Preparation of form A of (3R,4R.5S)-4-acetylamino-5-amino-3-(1-ethyl-propoxy)-cyclohex-1-enecarboxylic acid ethyl ester phosphate Form A may be formed upon spontaneous or seeded solution mediated phase transformation or upon spontaneous or seeded crystallization in organic solvents such as methanol, ethanol, acetonitrile, isopropanol, ethyl acetate, methyl acetate, isopropyl acetate, acetone, benzyl alcohol, methyl cyclohexane and others eventually mixture thereof or other low polarity solvents. Form A is obtained after drying. The accessibility may be influenced by the impurity profile of the compound and the choice of solvent.

Preparation of form B of (3R,4R,5S)-4-acetylamino-5-amino-3-(1-ethyl-propoxy)-cyclohex-1-enecarboxylic acid ethyl ester phosphate Form B may be formed by adding (3R,4R,5S)-4-acetylamino-5-amino-3-(1-ethyl-propoxy)-cyclohex-1-enecarboxylic acid ethyl ester to the phosphoric acid and cooling the supersaturated solution from 50° C. to −40° C. as fast as possible (without seeding).

Preparation of form C of (3R,4R,5S)-4-acetylamino-5-amino-3-(1-ethyl-propoxy)-cyclohex-1-enecarboxylic acid ethyl ester phosphate Crystalline form C of (3R,4R,5S)-4-acetylamino-5-amino-3-(1-ethyl-propoxy)-cyclohex-1-enecarboxylic acid ethyl ester phosphate may be formed by the method comprising following steps: step a) dissolving compound of formula (I) into water and adjusting pH to 4.0; step b) sterile filtering the solution through a sterilized 0.22 μm membrane; step c) aseptic filling the solution into sterile depyrogenated vial and stoppering the vial with a sterile stopper; step d) lyophilizing the solution in a steam-sterilized freeze-dryer.

An injectable pharmaceutical formulation may comprises a pharmaceutically effective amount of crystalline form C of compound of formula (I) and a pharmaceutically acceptable carrier.

Preparation of the amorphous form of (3R,4R,5S)-4-Acetylamino-5-amino-3-(1-ethyl-propoxy)-cyclohex-1-enecarboxylic acid ethyl ester phosphate Evaporation of a solution of (3R,4R,5S)-4-acetylamino-5-amino-3-(1-ethyl-propoxy)-cyclohex-1-enecarboxylic acid ethyl ester phosphate in organic solvents such as dichloromethane, ethyl acetate or others leading to amorphous solid state usually as a foam.

A amorphous form of (3R,4R,5S)-4-acetylamino-5-amino-3-(1-ethyl-propoxy)-cyclohex-1-enecarboxylic acid ethyl ester phosphate may surprisingly also be obtained by micronization of an initially crystalline sample of (3R,4R,5S)-4-acetylamino-5-amino-3-(1-ethyl-propoxy)-cyclohex-1-enecarboxylic acid ethyl ester phosphate in a agate ball mill.

Alternatively the amorphous form is obtained by spray drying a solution of (3R,4R,5S)-4-Acetylamino-5-amino-3-(1-ethyl-propoxy)-cyclohex-1-enecarboxylic acid ethyl ester phosphate in organic solvents such as ethanol.

The crystalline form(s) and the amorphous forms of the present invention can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described crystalline forms or the amorphous of the compounds of formula I, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the described crystalline forms or the amorphous of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 100 mg is effective. Depending on severity of the disease and the precise pharmacokinetic profile the crystalline forms or amorphous forms of the present invention could be administered with one or several daily dosage units, e.g. in 1 to 3 dosage units.

The pharmaceutical preparations conveniently contain about 1-500 mg, preferably 1-100 mg, of the crystalline form(s) or the amorphous forms of the compound of formula I.

To prepare the pharmaceutical preparations, containing the crystalline form(s) or the amorphous forms of the compound of formula I, these materials are often micronized. Micronization is a commonly used and well known process in the pharmaceutical industry to reduce the particle size of drug substances. The reason for micronization is usually to increase the bioavailability of the drug substance or to improve its overall technical processability.

The following examples illustrate the preparation of the polymorphic and amorphous material within the scope of the invention. These examples and preparations which follow are provided to enable those skilled in the art to more clearly understand and to practice the present invention. They should not be considered as limiting the scope of the invention, but merely as being illustrative and representative thereof.

EXAMPLE 1

Preparation of Crystalline form A of the Compound of Formula I 0.2 g of (3R,4R,5S)-4-acetylamino-5-amino-3-(1-ethyl-propoxy)-cyclohex-1-enecarboxylic acid ethyl ester phosphate was heated to reflux in the quantity of solvent stated in table 1 until it was dissolved. The solution was then allowed to cool slowly in an oil bath and then place in a refrigerator at approximately 4° C. overnight. All samples were dried in a vacuum at room temperature.

The crystals obtained were analyzed and did not exhibit significant differences between the samples and the reference substance.

TABLE 1

Experimental conditions of crystallization of form A of formula I

| Solvent (incl. temperatures range) | Volume of solvent |
|---|---|
| Ethanol (78° C. to RT) | 6.7 mL |
| Ethanol/acetone (59° C. to RT) | 16 mL/72 mL |
| Isopropanol (83° C. to RT) | 32.5 mL |
| Ethanol/ethyl acetate (77° C. to 4° C.) | 25 mL/40 mL |
| Methanol/acetonitrile (80° C. to 4° C.) | 16 mL/60 mL |
| Methanol/acetone (36° C. to 4° C.) | 2 mL/7 mL |
| Dimethyl formamide (125° C. to RT) | 1 mL |
| Benzyl alcohol/methyl cyclohexane (120° C. to 4 | 1 mL/5 mL |
| Ethanol (60° C. to RT) | 7 mL |
| Methanol/acetone (50° C. to RT) | 2 mL/7 mL |

Characterization of Crystal Form A

Form A can be characterized by an XRPD pattern obtained with a Cu Kα radiation having characteristic peaks expressed in degrees 2θ at approximately: approximately 5.1, 12.4, 13.0, 14.3, 15.2, 16.1, 19.0, 19.3, 20.3, 20.6, 21.6, 24.4 and 26.3 or by an infrared spectrum having sharp bands at approximately: 3352, 3162, 1724, 1663, 1623, 1551, 1376, 1337, 1263, 1173, 1132, 1071, 1027, 953, 880, 854, 731 cm$^{-1}$

EXAMPLE 2

Preparation of Crystalline Form B of the Compound of Formula I 16.9 g of phosphoric acid were mixed with 700 mL ethanol in a nitrogen purged 1000 mL glass reactor fitted with a mechanic stirrer and heated to 50 to 55° C. A solution of 45.8 g of (3R,4R,5S)-4-acetylamino-5-amino-3-(1-ethyl-propoxy)-cyclohex-1-enecarboxylic acid ethyl ester in 250 mL of ethanol was added to the phosphoric acid solution within 3 to 5 minutes under stirring. The result clear solution was cooled to −40° C. within 1 hour without seeding. The obtained crystal suspension was slowly stirred at −40° C. over night. The suspension was filtered and washed with 240 mL of acetone and 300 mL of n-heptane. The crystal was then dried in vacuum under maximal temperature of 50° C. 53 g of fine white crystal form B was obtained, correspond to a yield of 88.6%.

Characterization of Crystal Form B

Form B can be characterized by an XRPD pattern obtained with a Cu Kα radiation having characteristic peaks expressed in degrees 2 θ at approximately: approximately 5.3, 6.0, 7.4, 12.1, 12.8, 13.6, 16.1, 18.0, 18.7, 21.4, 23.8 and 24.3 or by an infrared spectrum having sharp bands at approximately: 3347, 3172, 2719, 1728, 1713, 1661, 1619, 1552, 1377, 1335, 1293, 1262, 1245, 1199, 1132, 1072, 1031, 968, 953, 938, 875, 851, 730 cm$^{-1}$.

EXAMPLE 3

Preparation of Crystalline form C of the Compound of Formula I

The bulk solution was prepared by dissolution of (3R,4R,5S)-4-acetylamino-5-amino-3-(1-ethyl-propoxy)-cyclohex-1-enecarboxylic acid ethyl ester phosphate into water for injection followed by pH adjustment with 0.1 N hydrochloric acid (HCl) to pH 4.0.

Before freeze-drying the bulk solution is sterile filtered through a sterilized 0.22 μm membrane filter using a nitrogen pressure of approx. 0.5 bar (maximum 0.7 bar). The filtrate is collected into a sterile depyrogenated vessel, for example consisting of borosilicate glass.

Under aseptic conditions, the sterile bulk solution is filled into sterile depyrogenated vials which are then stoppered with sterile stoppers in lyo-position and subsequently lyophilized in a steam-sterilized freeze-dryer.

After freeze-drying the vial headspace is overlaid with sterile filtered nitrogen, the vials are fully stoppered and finally sealed with aluminum flip-off caps.

The following lyophilisation cycle was developed.

| | Shelf temperature (° C.) | Ramp temperature (° C./min) | Ramp time (min) | Holding time (min) | Vacum (mTorr) |
|---|---|---|---|---|---|
| Pre-cooling | +5 | 0 | — | 60 | — |
| Freezing/ | −40 | 1 | 45 | 180 | — |
| Annealing | −5 | 1 | 35 | 240 | |
| | −40 | 1 | 30 | 120 | |
| Primary drying | −5 | 0.5 | 70 | 1100 | 200 |
| | Secondary drying optimal by −8° C. product temperature | | | | |
| Secondary drying | +30 | 0.5 | 54 | 300 | 100 |
| | | | 234 | 2000 | |
| Total process time | 2234 min = 37.2 hrs | | | | |

Characterization of Crystallin Form C

Form C can be characterized by an XRPD pattern obtained with a Cu Kα radiation having characteristic peaks expressed in degrees 2θ at approximately: approximately 4.5, 9.1 and 13.6. The term "approximately" means in this context that there is an uncertainty in the measurements of the degrees 2θ of ±0.2 degrees 2θ.

EXAMPLE 4

Crystalline Form C for use in Pharmaceutical Formulations

| | | |
|---|---|---|
| 60 mg | declared | filled (incl. 10% overfill) |
| Form C of the compound of formula I | 60-100-120 mg | 66-110-132 mg |
| HCl 0.1N ad pH 4.0 | q.s. | q.s. |
| Water for injection solutions | ad 1 mL | ad 1.2 mL |

Container: 3 ml flint glass, type I, 13 mm tubing glass vials

Closure: butyl rubber (D777-1), FPE laminated stopper, Aluminum flip-off 13 mm

The lyophilisate was dissolved with 1.1 mL sterile water for injection. The reconstituted solution contains 60, 100 and 120 mg/mL.

EXAMPLE 5

Preparation of the amorphous Form of the Compound of Formula I

A crystalline sample of (3R,4R,5S)-4-acetylamino-5-amino-3-(1-ethyl-propoxy)-cyclohex-1-enecarboxylic acid ethyl ester phosphate was milled for 45 minutes in a agate ball mill and then analyzed.

Characterization of the Amorphous Form

The amorphous form can be characterized by the lack of a Bragg diffraction peak in its XRPD pattern or by an infrared spectrum having bands at approximately: approximately 3257, 3180, 3070, 2401, 1717, 1658, 1555, 1301, 1246, 1199, 1127, 1063, 1030, 943, 875, 735 $cm^{-1}$.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A crystalline form C of (3R,4R,5S)-4-acetylamino-5-amino-3-(1-ethyl-propoxy)-cyclohex-1-enecarboxylic acid ethyl ester phosphate (I) which is characterized by an XRPD pattern comprising at least one X-ray diffraction peak (expressed in degrees 2θ) selected from the group consisting of approximately 4.5, approximately 9.1 and approximately 13.6.

2. The crystalline form C according to claim 1, wherein XRPD pattern comprising at least of two X-ray diffraction peaks (expressed in degrees 2θ) selected from the group consisting of approximately 4.5, approximately 9.1 and approximately 13.6.

3. The crystalline form C according to claim 1, wherein XRPD pattern comprising three X-ray diffraction peaks (expressed in degrees 2θ) selected from the group consisting of approximately 4.5, approximately 9.1 and approximately 13.6.

4. A method for therapeutic treatment and/or prophylaxis of a disease associated with a viral neuramidase comprising administering a therapeuicallly effective amount to a patient in need thereof of a crystalline form C of (3R,4R,5S)-4-acetylamino-5-amino-3-(1-ethyl-propoxy)-cyclohex-1-en-ecarboxylic acid ethyl ester phosphate (I) according to claim 1.

5. A pharmaceutical composition containing a crystalline form C of (3R,4R,5S)-4-acetylamino-5-amino-3-(1-ethyl-propoxy)-cyclohex-1-enecarboxylic acid ethyl ester phosphate (I) according to claim 1 and at least one pharmaceutically acceptable carrier, diluent or excipient.

6. An injectable pharmaceutical formulation comprising a composition according to claim 5 and a pharmaceutically acceptable carrier.

7. An injectable pharmaceutical formulation according to claim 6, which formulation contains 60 to 120 mg of Form C of compound of formula (I) dissolved in an aqueous solution at a pH of 3.0 to 7.0.

8. An injectable pharmaceutical formulation according to claim 7, which formulation contains Form C of compound of formula (I) dissolved in an aqueous solution at a pH of 3.5 to 4.5.

9. A method for preparing the crystalline form C of 3R,4R,5S)-4-acetylamino-5-amino-3-(1-ethyl-propoxy)-cyclohex-1-enecarboxylic acid ethyl ester phosphate (I) according to claim 1 comprising the step s of:
(a) dissolving a compound of formula I into water and adjusting pH to 4.0 with 0.1 N hydrochloric acid;
(b) sterile filtering the solution through a sterilized 0.22 μm membrane;
(c) aseptic filling the solution into sterile depyrogenated vial and stoppering the vial with a sterile stopper; and,
(d) lyophilizing the solution in a steam-sterilized freeze-dryer.

* * * * *